US009820856B2

(12) United States Patent
Guidera et al.

(10) Patent No.: US 9,820,856 B2
(45) Date of Patent: *Nov. 21, 2017

(54) SYSTEM AND METHOD FOR JOINT ARTHROPLASTY

(75) Inventors: Michael Guidera, Roseville, CA (US); Michael A. Serra, Cameron Park, CA (US); Daniel F. Justin, Orlando, FL (US); Chad W. Lewis, Layton, UT (US)

(73) Assignee: Consensus Orthopedics, Inc., El Dorado Hills, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/086,747

(22) Filed: Apr. 14, 2011

(65) Prior Publication Data

US 2011/0190897 A1  Aug. 4, 2011

Related U.S. Application Data

(63) Continuation of application No. 11/558,271, filed on Nov. 9, 2006, now Pat. No. 7,947,082.

(51) Int. Cl.
*A61F 2/38* (2006.01)
*A61F 2/30* (2006.01)

(52) U.S. Cl.
CPC ............ *A61F 2/3868* (2013.01); *A61F 2/389* (2013.01); *A61F 2002/305* (2013.01);
(Continued)

(58) Field of Classification Search
CPC . A61F 2/3868; A61F 2002/2892; A61F 2/389
(Continued)

(56) References Cited

U.S. PATENT DOCUMENTS

| 4,224,697 A | 9/1980 | Murray et al. |
| 4,822,366 A | 4/1989 | Bolesky |

(Continued)

FOREIGN PATENT DOCUMENTS

| EP | 0636353 | 7/1994 |
| EP | 0636353 | 2/1995 |

(Continued)

OTHER PUBLICATIONS

Jones, R; *Mobile Bearings in Revision of Total Knee Arthroplasty*, American Academy of Orthopaedic Surgery. Instructional course lectures.2005; 54 p. 225-231.

(Continued)

*Primary Examiner* — Thomas J Sweet
*Assistant Examiner* — Megan Wolf
(74) *Attorney, Agent, or Firm* — Pandiscio & Pandiscio

(57) ABSTRACT

An orthopedic joint prosthesis may include a first component, a bearing component, and a third component. The first component has a base and a keel protruding from the base to extend into a first bone. The keel's longitudinal axis is offset from a geometric center of the base. The base has a first articular surface and the bearing component has a second articular surface shaped to articulate with the first articular surface. A feature unitary with the first component reversibly attaches to the bearing component. The bearing component has a third articular surface shaped to articulate with a fourth articular surface on the third component. A distraction feature of the bearing component is shaped to provide alignment and/or distraction between the first articular surface and the fourth articular surface during insertion of the bearing component into a joint space between the first and second bones.

14 Claims, 12 Drawing Sheets

(52) U.S. Cl.
CPC .............. *A61F 2002/30383* (2013.01); *A61F 2002/30616* (2013.01); *A61F 2002/30878* (2013.01)

(58) Field of Classification Search
USPC .................... 623/14.12, 20.14, 20.15, 20.21, 623/20.32–20.34, 20.28, 20.29
See application file for complete search history.

(56) References Cited

U.S. PATENT DOCUMENTS

| | | | |
|---|---|---|---|
| 5,271,737 A | | 12/1993 | Baldwin et al. |
| 5,387,240 A | | 2/1995 | Pottenger et al. |
| 5,658,342 A | | 8/1997 | Draganich et al. |
| 5,658,344 A | | 8/1997 | Hurlburt |
| 5,871,543 A | | 2/1999 | Hofmann |
| 5,928,286 A | * | 7/1999 | Ashby et al. .............. 623/20.33 |
| 6,039,764 A | | 3/2000 | Pottenger |
| 6,123,728 A | | 9/2000 | Brosnahan et al. |
| 6,203,576 B1 | | 3/2001 | Afriat et al. |
| 6,296,666 B1 | | 10/2001 | Gardner |
| 6,319,283 B1 | | 11/2001 | Insall et al. |
| 6,428,577 B1 | | 8/2002 | Evans et al. |
| 6,494,915 B1 | | 12/2002 | Villar Gonzalez et al. |
| 6,623,526 B1 | * | 9/2003 | Lloyd ........................ 623/20.28 |
| 6,660,039 B1 | | 12/2003 | Evans et al. |
| 7,947,082 B2 | * | 5/2011 | Guidera et al. ............ 623/20.33 |
| 2003/0153980 A1 | | 8/2003 | Brack |
| 2004/0034432 A1 | | 2/2004 | Hughes et al. |
| 2005/0055102 A1 | * | 3/2005 | Tornier et al. .............. 623/20.32 |
| 2005/0209702 A1 | | 9/2005 | Todd et al. |
| 2011/0190897 A1 | | 8/2011 | Guidera et al. |

FOREIGN PATENT DOCUMENTS

| | | |
|---|---|---|
| EP | 1169980 | 7/2000 |
| EP | 1169980 | 3/2008 |
| IT | 1264820 | 7/1993 |

OTHER PUBLICATIONS

Dennis D; *Kinematics of Mobile-Bearing Total Knee Arthroplasty*. American Academy of Orthopedic Surgeons, Instructional course lectures. 2005; 54: p. 207 220.

Vertullo, Christopher J.; *Mobile Bearing in Primary Knee Arthroplasty*. J Am Acad Orthop Surg 2001; 9:355-364.

Insall John N.; *Meniscal-Bearing Knee Replacement*. Surgery of the Knee, Chapter 80; pp. 1717-1738, 2001.

Zimmer; *NexGen Mobile Bearing Knee*, www.zimmer.co.uk 2006.
Zimmer; *Comprehensive Natural-Knee Family*, www.zimmer.co.uk 2006.
Zimmer; *MBK*. www.zimmer.co.uk 2006.
Zimmer; *Innex*, www.zimmer.co.uk 2006.
Stryker; *Product Overview Catal.* pp. 1-36, 2003.
Industry. Orthopaedics; *Who is Doing What in Industry in the UK in Orthopaedic Devices & Material*. 2005 directory Version 1.1, pp. 1-50.
Stryker; *Scorpio CR and PS Femoral Components and Scorpio Tibial Tray with Titanium Plasma Sprayed Coating*. FDA 510(k) Summary, pp. 1-8, 2002.
Stryker; *Interax ISA*. Product Brochure, p. 1-6, 2000.
Johnson & Johnson; *LCS Complete Mobile-Bearing Knee System*. Website: www.jnjgateway.com 2000.
Howmedica Osteonics; *Scorpio Low Profile Tibial Tray*. 510K Submisson, 2003.
Jones, R., Mobile Bearings in Revision Total Knee Arthroplasty, American Academy of Orthopaedic Surgery, Institutional Course Lectures, 2005, pp. 225-231.
Dennis, O., Kinematics of Mobile-Bearing Total Knee Arthroplasty, American Academy of Orthopedic Surgeons, Institutional Course Lectures, 2005, pp. 207-220.
Vertullo, Christopher J., Mobile Bearings in Primary Knee Arthroplasty, The Journal of the American Academy of Orthopaedic Surgeons, 2001, pp. 355-364.
Insall, John N., Meniscal-Bearing Knee Replacement, Surgery of the Knee, Chapter 80, pp. 1717-1738.
Zimmer, NexGen Mobile Bearing Knee, www.zimmer.co.uk.
Zimmer, Comprehensive Natural-Knee Family, www.zimmer.co.uk.
Zimmer, MBK, www.zimmer.co.uk.
Zimmer, Innex, www.zimmer.co.uk.
. Stryker, Scorpio+. Product Insert, pp. 1-2.
Stryker, Product Overview Catal, pp. 1-36.
Industry. Orthopaedics; Who Is Doing What in Industry in the Uk in Orthopaedic Devices and Material, 2005, pp. 1-50.
Stryker, Scorpio CR and PS Femoral Components and Scorpio Tibial Try With Titanium Plasma Sprayed Coating, FDA 510(k) Summary, pp. 1-8.
Stryker, Interax ISA, Product Brochure, pp. 1-6.
Johnson&Johnson, LCS Complete Mobile-Bearing Knee System, www.jnjgateway.com.
Howmedica Osteonics, Scorpio Low Profile Tibial Tray, 510K Submission.
Depuy/Johnson&Johnson, LCS Complete Mobile-Bearing Knee System, O.R. Reference Chart, pp. 1-3.

* cited by examiner

SYSTEM AND METHOD FOR JOINT ARTHROPLASTY

CROSS-REFERENCE TO RELATED APPLICATIONS

This application is a continuation of:

U.S. patent application Ser. No. 11/558,271, filed Nov. 9, 2006, now U.S. Pat. No. 7,947,082, and is entitled SYSTEM AND METHOD FOR JOINT ARTHROPLASTY, which is incorporated herein by reference.

The following disclosure is incorporated herein by reference:

U.S. application Ser. No. 07/940,441, filed Sep. 4, 1992, now U.S. Pat. No. 5,271,737, which is entitled TIBIAL PROSTHETIC IMPLANT WITH OFFSET STEM.

BACKGROUND OF THE INVENTION

1. The Field of the Invention

The present invention relates generally to orthopaedic medicine, and more particularly, to knee arthroplasty.

2. The Relevant Technology

Current orthopaedic prostheses have many problems, including incompatibility with mating prepared bone surfaces, the inevitable wear of the prosthesis, and inability to mimic the native joint biomechanics. Fixed-bearing knee prostheses (e.g., the meniscal prosthesis is fixed relative to the tibial prosthesis) have been shown to have greater wear rates compared to mobile-bearing prosthesis (e.g., the meniscal prosthesis is movable relative to the tibial prosthesis). In addition, mobile-bearing prostheses are likely to mimic native joint biomechanics more closely than fixed-bearing prostheses. Known mobile-bearing knee prosthesis components typically are not fully optimized to maximize bone purchase and fixation, while minimizing native tissue damage or resection.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to orthopaedic medicine, and in particular, to total knee arthroplasty. Those of skill in the art will recognize that the systems and methods described herein may be readily adapted for any total joint arthroplasty procedure.

Figure 1:
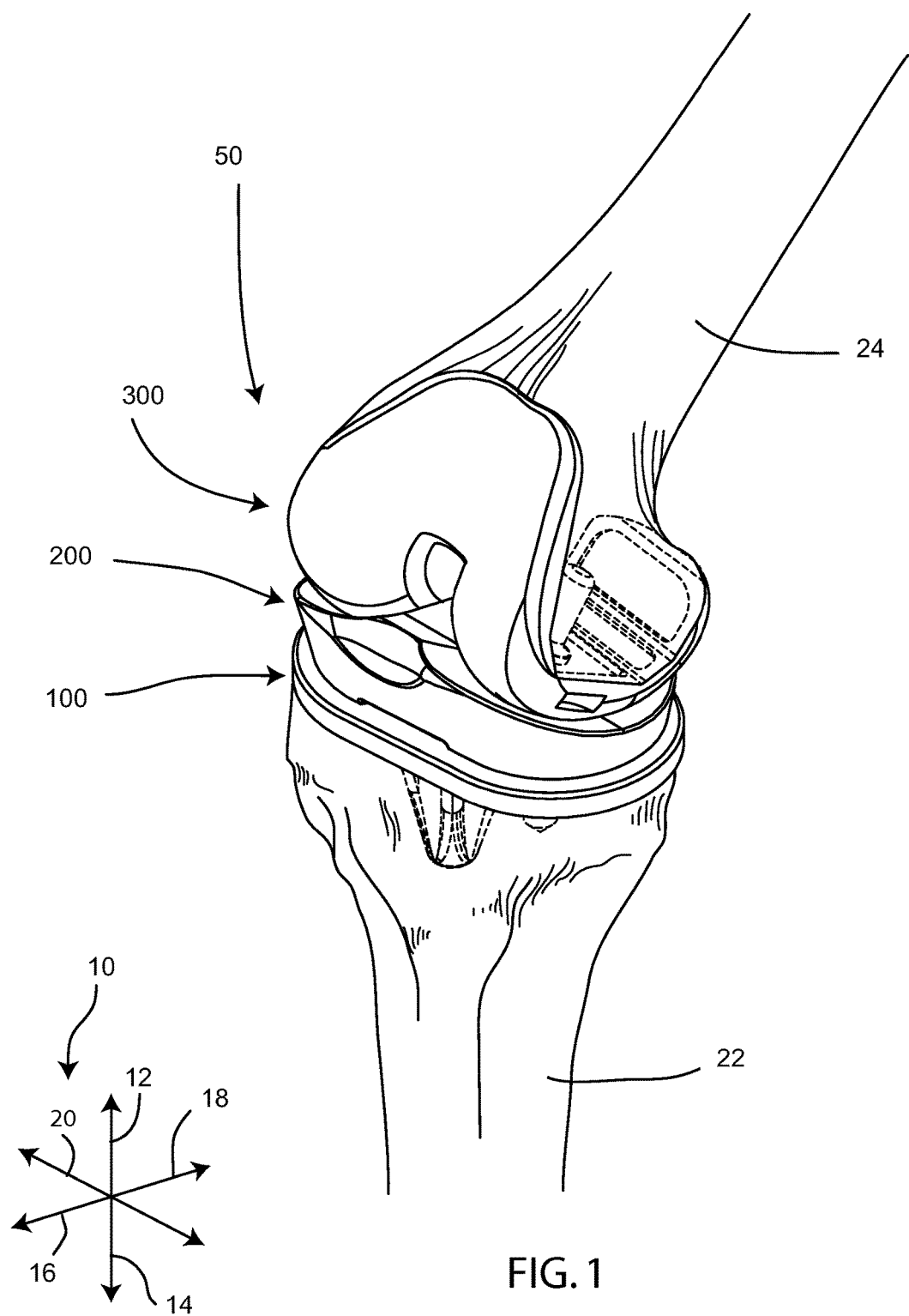
FIG. 1 is a perspective view of a mobile bearing knee prosthesis according to one embodiment of the invention.

Referring to FIG. 1, an antero-lateral perspective view illustrates a mobile bearing knee prosthesis 50 according to one embodiment of the invention, implanted in a knee. This figure and subsequent figures may be oriented according to the reference arrow diagram 10, having a proximal direction 12, a distal direction 14, an anterior direction 16, a posterior direction 18, and a medial/lateral axis 20. In this application, "left" and "right" are used with reference to a posterior view. "Medial" refers to a position or orientation toward a sagittal plane (i.e., plane of symmetry that separates left and right sides of the body from each other), and "lateral" refers to a position or orientation relatively further from the sagittal plane.

The prosthesis 50 has three components: a first component 100, a bearing component 200, and a third component 300. In this embodiment of the invention, the first component 100 is a tibial tray, which is implanted into a prepared proximal end of a first bone 22, in this example a tibia. The third component 300 is implanted into a prepared distal end of a second bone 24, in this example a femur. The bearing component 200 is attached onto the first component 100, and provides a bearing surface which maximizes contact with both the first component 100 and the third component 300.

Figure 2:
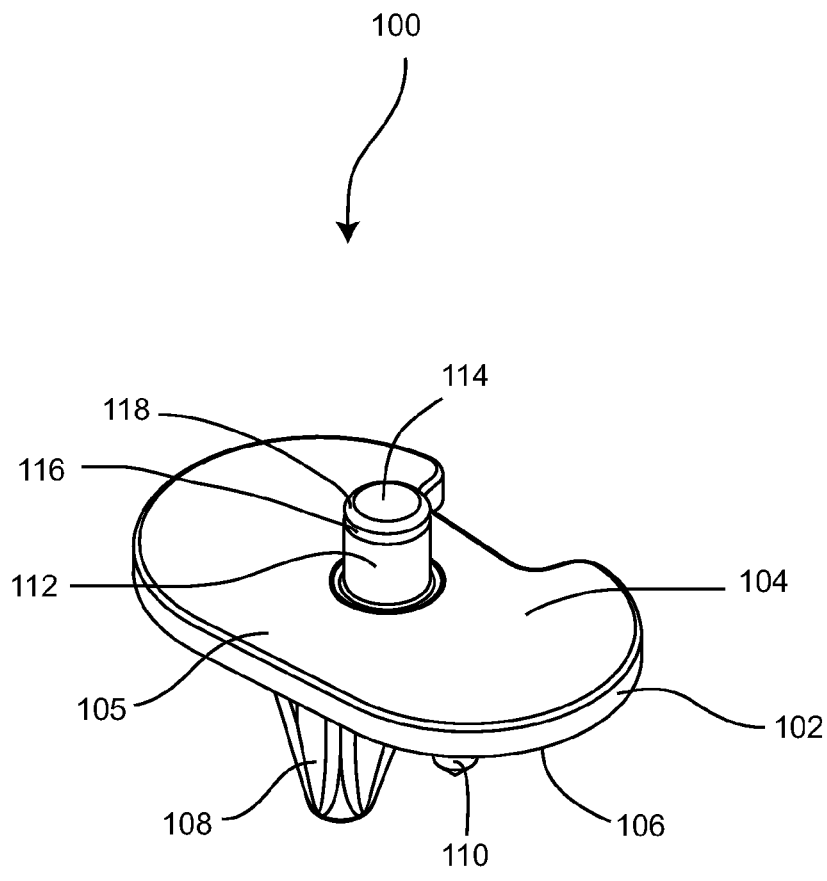
FIG. 2 is a perspective view of a first component of the mobile bearing knee prosthesis of FIG. 1.
Figure 2:
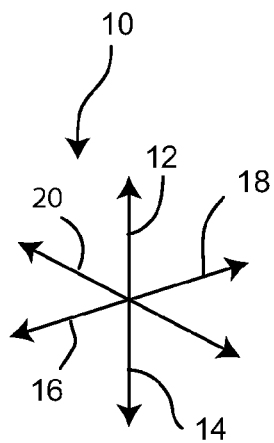

Referring to FIG. 2, a perspective view illustrates the first component 100. The keel offset illustrated in this and other figures may be similar to that invented by Baldwin, et al. in U.S. Pat. No. 5,271,737, which patent is hereby incorporated herein by reference. The first component 100 may comprise cobalt, chrome, molybdenum, titanium, polymers, mixtures thereof, or any other materials that are known to be useful implant materials in the orthopaedic arts. The first component 100 comprises a non-symmetrical ovoid plate 102 with a flat bearing-facing side 104 and a bone-facing side 106. The bearing-facing side 104 has a first articulating surface 105 which articulates with the bearing insert 200.

Extending distally from the bone-facing side 106 is a keel 108, by which the first component 100 is affixed to the prepared bone. In this embodiment of the invention, the keel 101 is offset, in both the anterior-posterior and medial-lateral directions, from the center of the bone-facing side 106 so that it does not extend into the cortical material of the bone. Also extending distally from the bone-facing side 106 is a plurality of pegs 110, which will be more clearly illustrated subsequently.

Protruding from the bearing-facing side 104 is a unitary columnar post 112. The post 112 is generally centered on the bearing-facing side 104, but it can also be offset along the anterior, posterior, and/or medial-lateral directions 16, 18, 20 to correspond to the joint's longitudinal rotation axis. The post 112 protrudes from the bearing-facing side 104 to a variable length which is long enough to retain the bearing component 200, and terminates at a proximal end 114.

Near the proximal end 114 is an annular groove 116 which is narrower in diameter than the remainder of the post 112. Immediately above the annular groove 116 is an annular ridge 118, whose diameter is wider than that of the groove 116 and the remainder of the post 112. The annular groove 116 and annular ridge 118 form part of a unitary snap feature which securely and reversibly attaches the bearing component 200 to the first component 100 while simultaneously allowing the bearing component 200 some freedom to rotate relative to the first component 100. In other embodiments, the bearing component may translate or translate and rotate relative to the first component. One such embodiment will be shown and described subsequently, in connection with FIGS. 10, 11, and 12.

Figure 3:
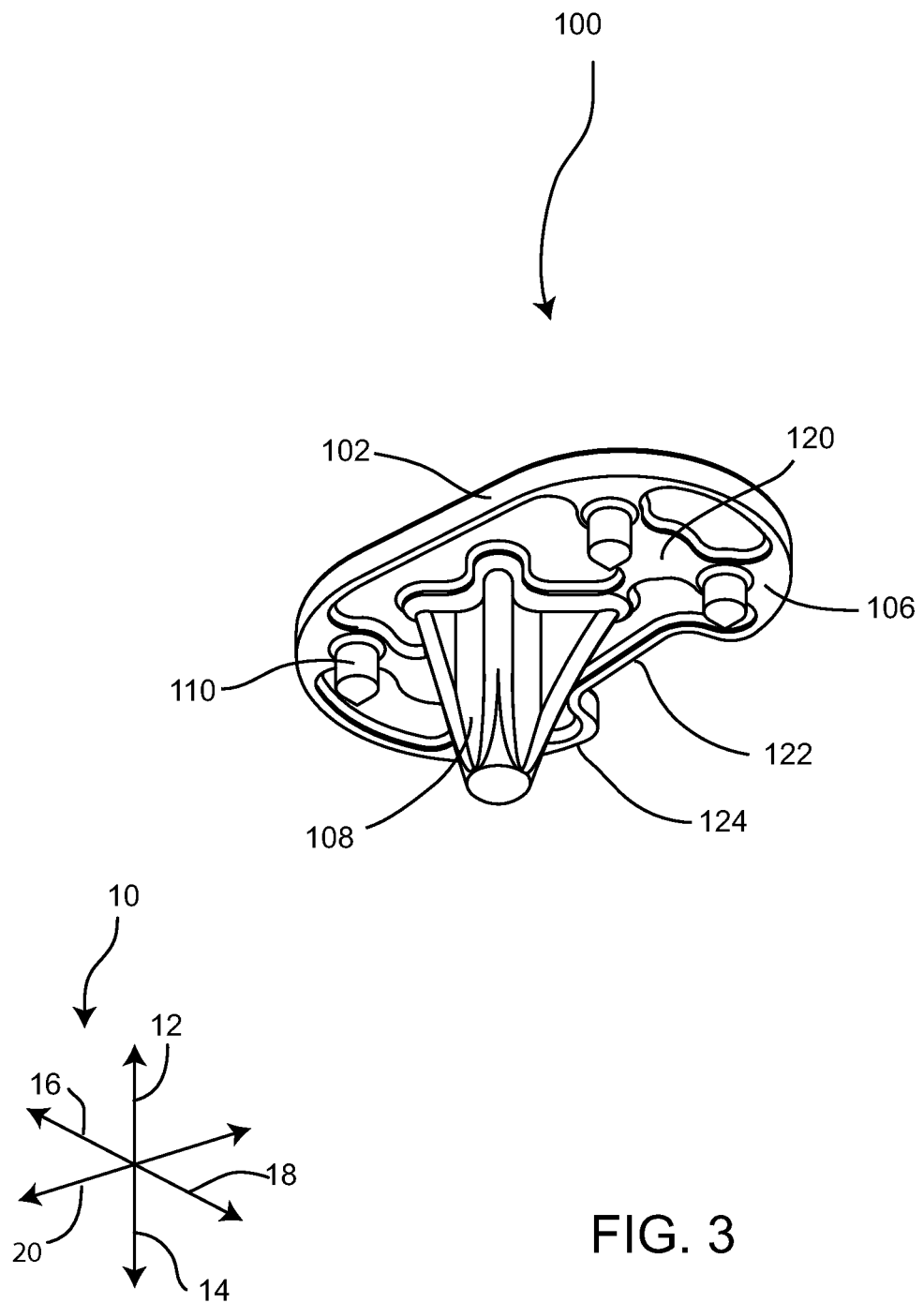
FIG. 3 is a perspective view of the first component of FIG. 2.

Referring to FIG. 3, a perspective view illustrates the bone-facing side 106 of the first component 100. The bone-facing side 106 has a bone-facing surface 120. The bone-facing surface 120, keel 108 and pegs 110 may comprise a porous material that encourages bone ingrowth. A notch 122 is indented into a posterior side 124 of the plate 102 in this embodiment, to allow room for retainment of the posterior cruciate ligament (PCL) or another ligament behind the plate 102.

In other embodiments of the invention, the first component 100 can vary according to the joint being replaced or the specific anatomy of the patient. For example, the dimensions and surface area of the plate 102 can vary, as can the size and placement of the keel 108, and the height, diameter and placement of the post 112. The pegs 110 may be present or absent. The notch 122 may vary in size, shape, and placement, or be absent as in the case of a PCL sacrificing insert.

Figure 4:
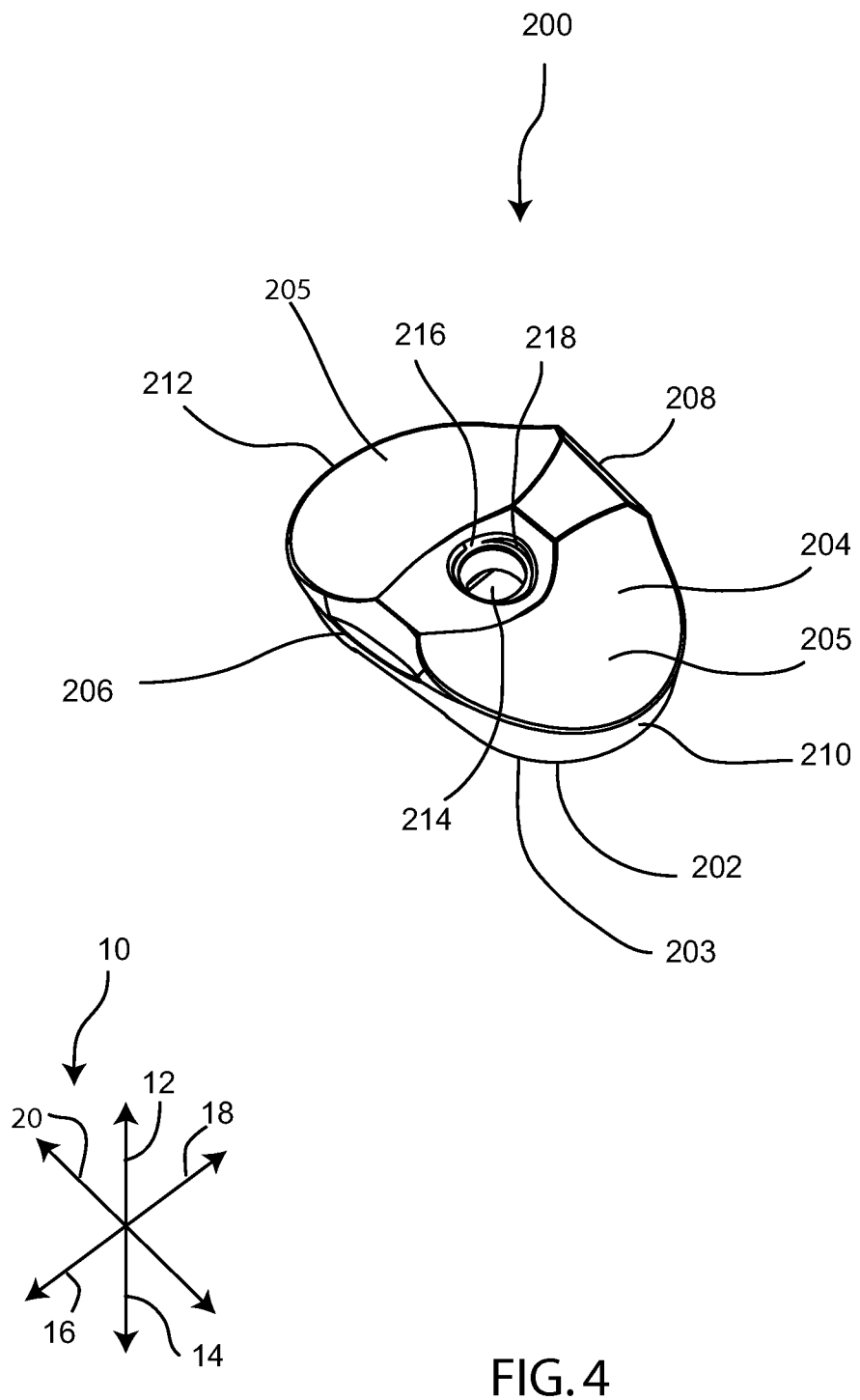
FIG. 4 is a perspective view of a bearing component of the mobile bearing knee prosthesis of FIG. 1.

Referring to FIG. 4, a perspective view of the bearing component 200 is shown. The bearing component 200 has a first component facing side 202 with a second articulating surface 203 and a third component facing side 204 with a third articulating surface 205, which is divided into medial and lateral portions. It has an anterior end 206, a posterior end 208, a medial end 210 and a lateral end 212. The third articulating surface 205 is sculpted and curved to align with the third component 300 when the prosthesis 50 is implanted in the patient. In the event that a hemiarthroplasty, rather than a full arthroplasty, is desired, the third articulating surface 205 may instead articulate with the natural distal end of the femur.

A bore 214 is generally centrally located, extending through the bearing component 200 from the first component facing side 202 to the third component facing side 204. The bore 214 is positioned to fit over the post 112 of the first component, allowing the flat first component facing side 202 to align with the flat bearing facing side 104 when the bearing component 200 is reversibly attached to the first component 100. Immediately adjacent to where the bore 214 opens to the third component facing side 204, the diameter of the bore 214 is greater, forming a circular groove 216. Just below the groove 216 in a distal direction is a circular rim 218, where the diameter of the bore 214 is wider than in the groove 216. The bearing component rim 218 reversibly retains the bearing component 200 relative to the first component 100 because the annular ridge 118 seats against the shoulder defined by the rim 218.

In the embodiment illustrated, a height of the anterior end 206 is higher than a height of the posterior end 208. This configuration allows increased anterior stability with the third component 300. An alternate bearing component configuration (not shown), in which the heights of the anterior 206 and posterior 208 ends are closer to equal, provides equal stability, between the anterior and posterior ends of the bearing component 200.

Figure 5:
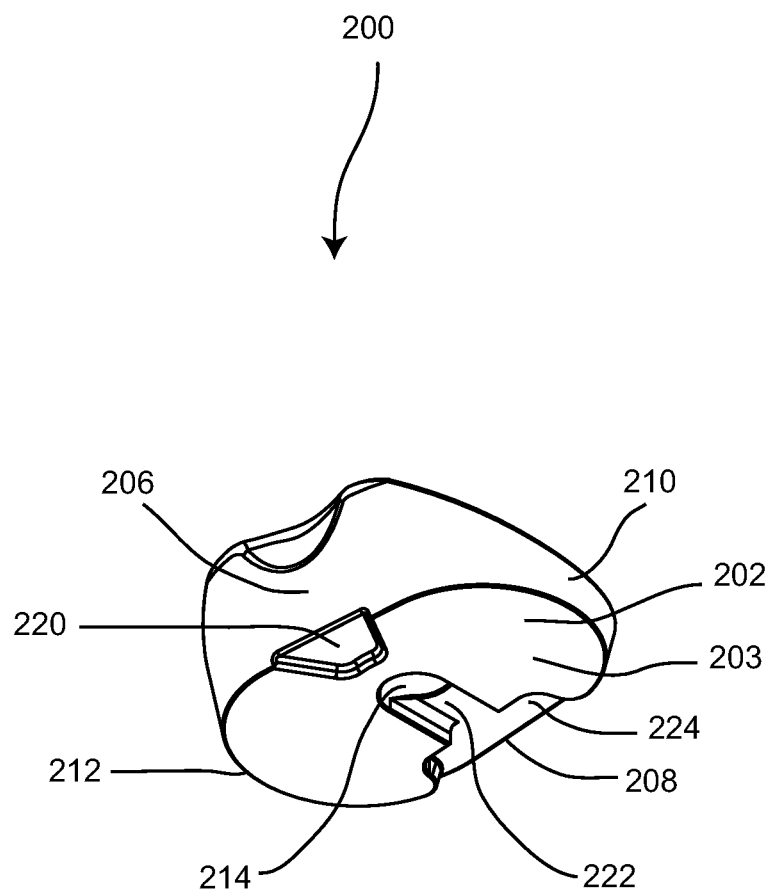
FIG. 5 is a perspective view of the bearing component of FIG. 4.

Referring to FIG. 5, a perspective view of the bearing component 200 is shown. Where the first component facing side 202 meets the anterior end 206, an instrument slot 220 is formed as a depression in the second articulating surface 203. The instrument slot 220 allows insertion of a wedge instrument (not shown) to pry the bearing component 200 from the first component 100. A channel 222, which is a groove indented into the second articulating surface 203, extends from the bore 214 to generally the posterior end 208. The channel 222 may be ramped such that the depth of the channel varies between the posterior end 208 and the bore 214. The channel configuration allows the bearing component 200 to self-align as it is slid in an anterior to posterior direction into place over the post 112, with a minimum of distraction of the joint. In addition, the channel configuration allows the bearing component to be more easily removed during bearing replacement, with minimum joint distraction.

Near the posterior end of the channel 222, a cutout 224 abuts the channel 222 on both sides. The cutout 224 is a depression in the second articulating surface 203 along the posterior end 208 extending from both sides of the channel 222 along the medial-lateral axis. The cutout 224 may be shallower than, or as deep as, the channel 222, and may or may not include a notch for the PCL. The purpose of the cutout 224 is to prevent creep of the bearing insert material over time by distributing the stress on the insert 200 to where it is in surface contact with the first component 100.

The bearing component 200 may be formed of ultra-high molecular weight polyethylene (UHMWPE), but may, in alternative embodiments, comprise a different polymer, a cross linked polymer, or an interpenetrating polymer network (e.g., comprising of hyaluronic acid), or an HIP processed polymer material. Alternatively, the bearing component 200 may comprise a combination of metallic and non-metallic materials, such as a metal base with a polymer top.

Figure 6:
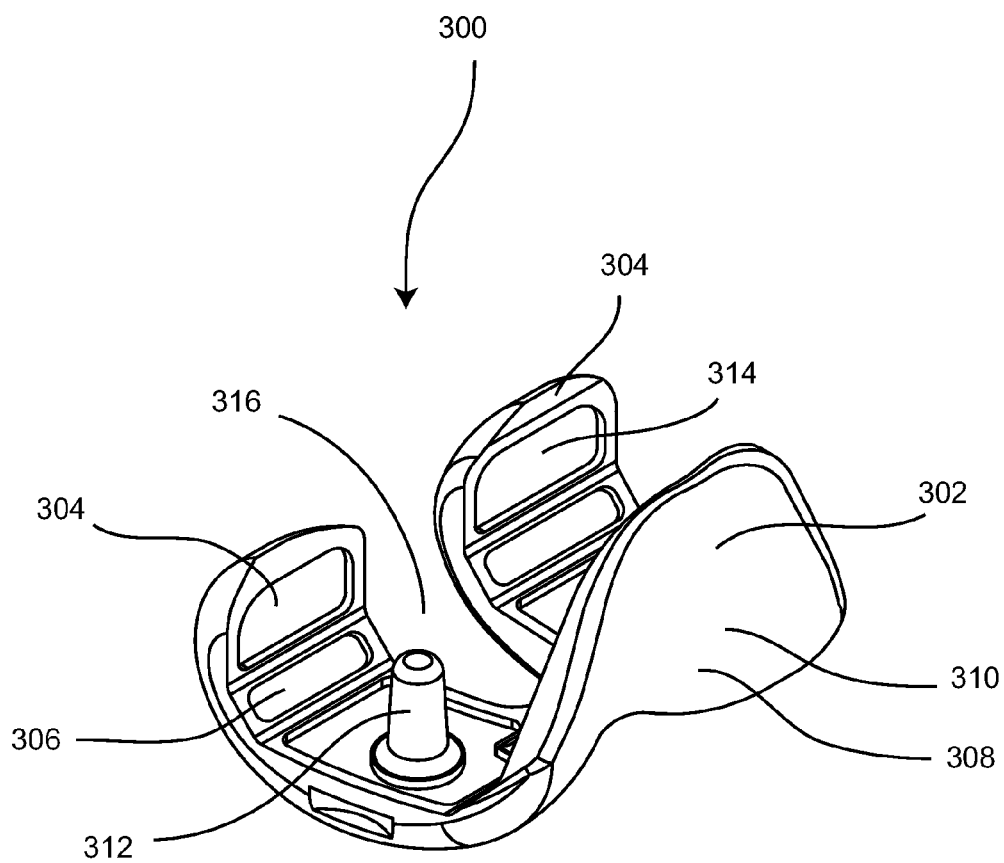
FIG. 6 is a perspective view of a third component of the mobile bearing knee prosthesis of FIG. 1.
Figure 6:
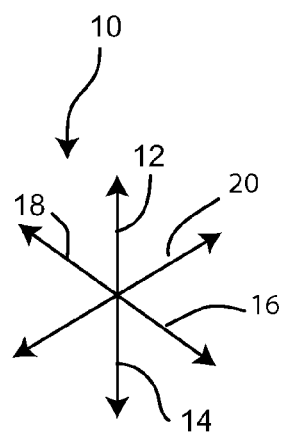

Referring to FIG. 6, a perspective view of the third component 300 is shown. In this embodiment of the invention, a femoral component is depicted, but in other embodiments, the third component 300 may be a femoral component, a natural knee, or a bone of another joint. The third component 300 has a curved V shape, with a trochlear groove 302 adjoining two condyles 304 extending posteriorly and then curving cephalically, to match the contours of a natural distal end of a femur. The trochlear groove 302 and condyles 304 have a bone-facing side 306, and a bearing-facing side 308 which has a fourth articulating surface 310. The radius of the curvature of the condyles 304 relatively matches the contours of the third articulating surface 205 on the bearing component 200.

Extending proximally from the bone-facing side 306 of each condyle 304 is a stem 312, which is configured to be driven into a prepared second bone, or a femur in this embodiment. The bone-facing side 306 has a bone-facing surface 314 which may comprise a porous material to encourage bone ingrowth. A gap 316 between the condyles 304 is generally a fixed height, but the condyles 304 may be of various widths, sizes and curvatures depending on the specific anatomy of the patient or bearing component 200. The surface curvature of the condyles 304 may also vary to match the curvature of the specific bearing component 200 chosen for the patient's mobility requirements.

Figure 7:
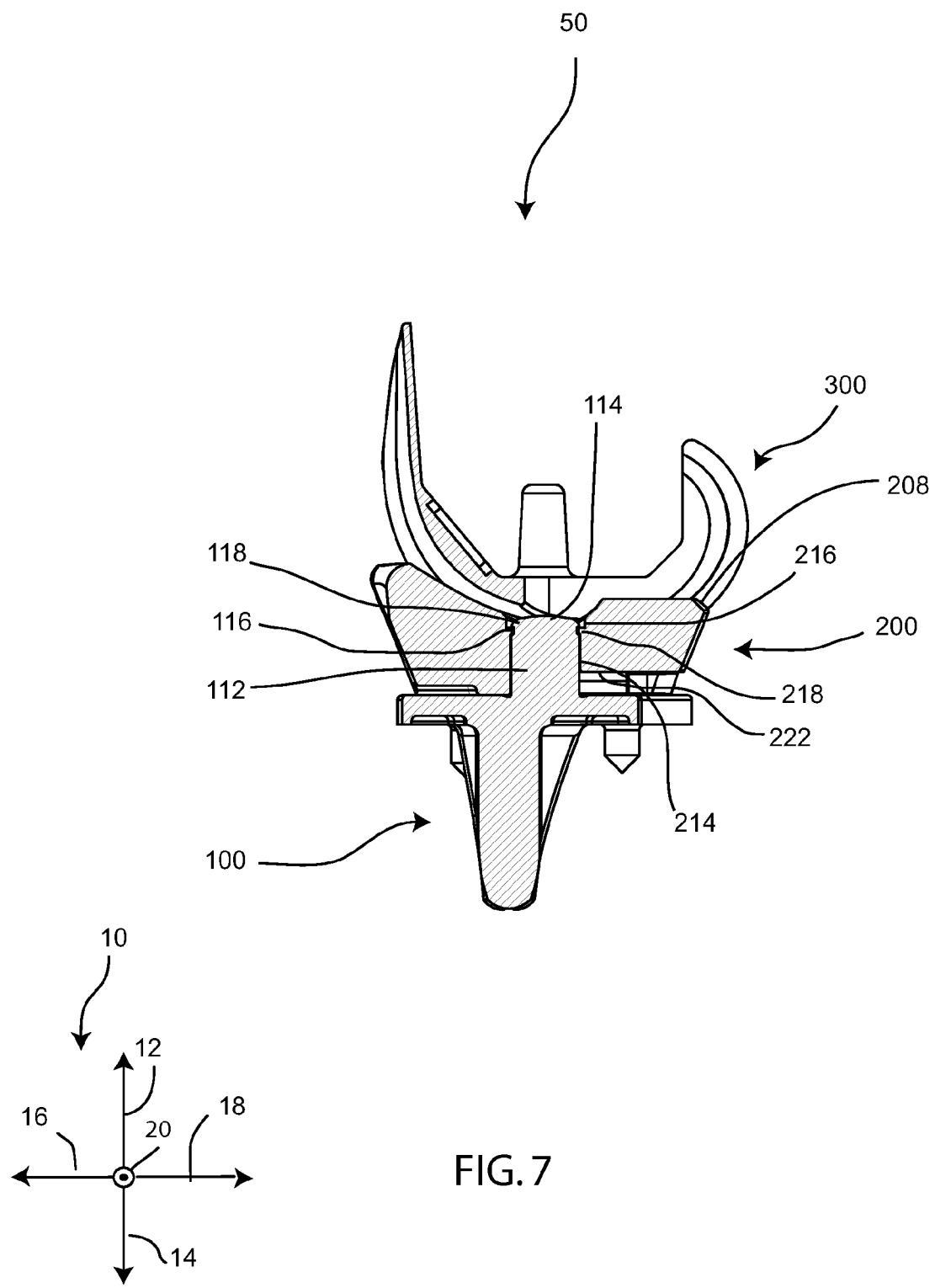
FIG. 7 is a sagittal cross-section view of the mobile bearing knee prosthesis of FIG. 1.

Referring to FIG. 7, a sagittal cross-section of the prosthesis 50 is shown. During the implantation procedure, the first component 100 may first be implanted in the first bone. Next, the bearing component 200 is reversibly attached onto the first component 100 and lastly the third component 300 is implanted in the second bone, which may be a femur. Alternatively, the order of implantation of the last two components (the bearing component 200 and the third component 300) may be reversed.

When the bearing component 200 is snapped into engagement (i.e., reversibly attached) with the first component 100, it is slid in an anterior to posterior direction with the channel 222 sliding over the proximal end 114 of the post 112, until the bore 214 slips over the post 112. The bore 214 slides down the post 112 until resistance is encountered as the rim 218 meets the ridge 118. The bearing component 200 is pushed until the rim 218 deforms and snaps past the ridge 118, and the rim 218 rests in the annular groove 116 of the post 112 while the ridge 118 rests in the groove 216 of the bore 214. Thus reversibly attached together, the bearing component 200 remains engaged with the first component 100 until pried apart by the wedge tool (not shown). However, the engagement is loose enough to allow movement of the bearing component 200 relative to the first component 100. Movement between the bearing component 200 and the first component 100 allows the bearing component 200 to more readily align with the third component 300. This provides increased area contact, and reduced point contact, thereby reducing wear and other mechanical failure between the bearing component 200 and the third component 300.

Figure 8:
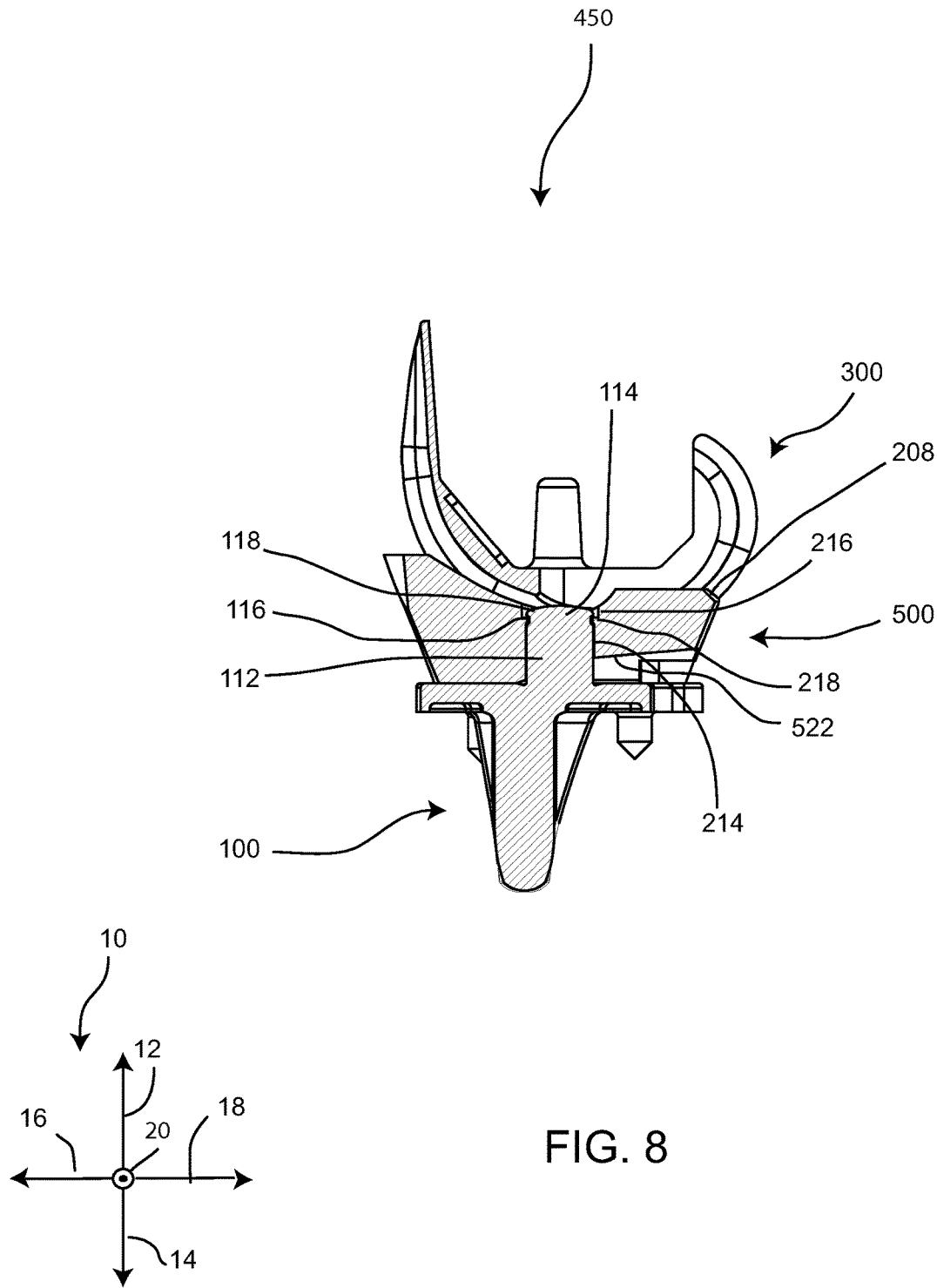
FIG. 8 is a sagittal cross-section view of the mobile bearing knee prosthesis of FIG. 1 illustrating an alternative embodiment of the bearing component.

Referring to FIG. 8, a sagittal cross-section illustrates a prosthesis 450 according to an alternative embodiment of the invention. The prosthesis 450 is similar to the prosthesis 50 described previously, except that the prosthesis 450 has a bearing component 500 with a configuration different from that of the bearing component 200. More precisely, a channel 522, which is a groove indented into the second articulating surface 203, extends from the bore 214 to generally the posterior end 208 of the bearing component 500. The channel 522 is ramped such that the depth of the channel 522 varies between the posterior end 208 and the bore 214.

The ramped shape of the channel 522 helps to provide alignment and/or distraction between the first and fourth articulating surfaces 105, 310 during insertion of the bearing component 500 into a joint space between the first and second bones. The configuration of the channel 522 allows the bearing component 500 to self-align as it is slid in an anterior to posterior direction into place over the post 112, with a minimum of distraction of the joint. In addition, the configuration of the channel 522 allows the bearing component 500 to be more easily removed during bearing replacement, with minimum joint distraction.

Figure 9:
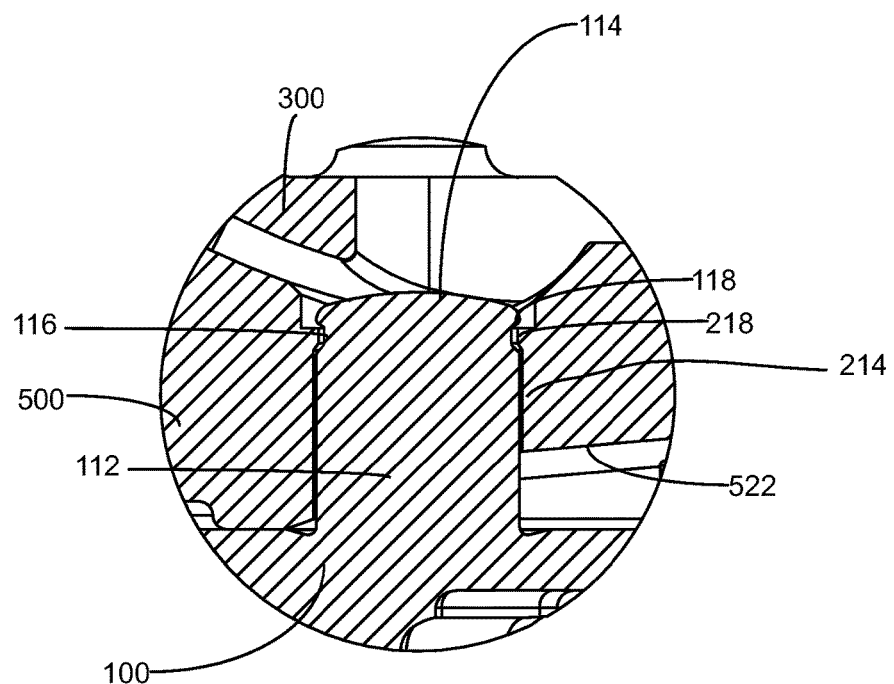
FIG. 9 is an enlarged sagittal cross-section view of the mobile bearing knee prosthesis of FIG. 8 illustrating the unitary feature.
Figure 9:
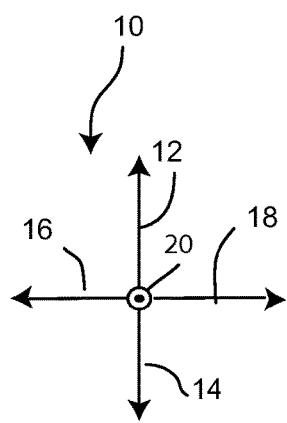

Referring to FIG. 9, an enlarged sagittal cross-sectional view illustrates a portion of the prosthesis 450, in particular the reversible attachment mechanism between first component 100 and bearing component 500. As the bearing component 500 is reversibly attached to the first component 100, it is slid in an anterior to posterior direction with the channel 222 sliding over the proximal end 114 of the post 112, until the bore 214 slips over the post 112. The bore 214 slides down the post 112 until resistance is encountered as the rim 218 meets the ridge 118. The bearing component 200 is pushed until the rim 218 deforms and deforms past the ridge 118, and the rim 218 rests in the annular groove 116 of the post 112 while the ridge 118 rests in the groove 216 of the bore 214. Thus reversibly attached together, the bearing component 500 remains engaged with the first component 100.

Figure 10:
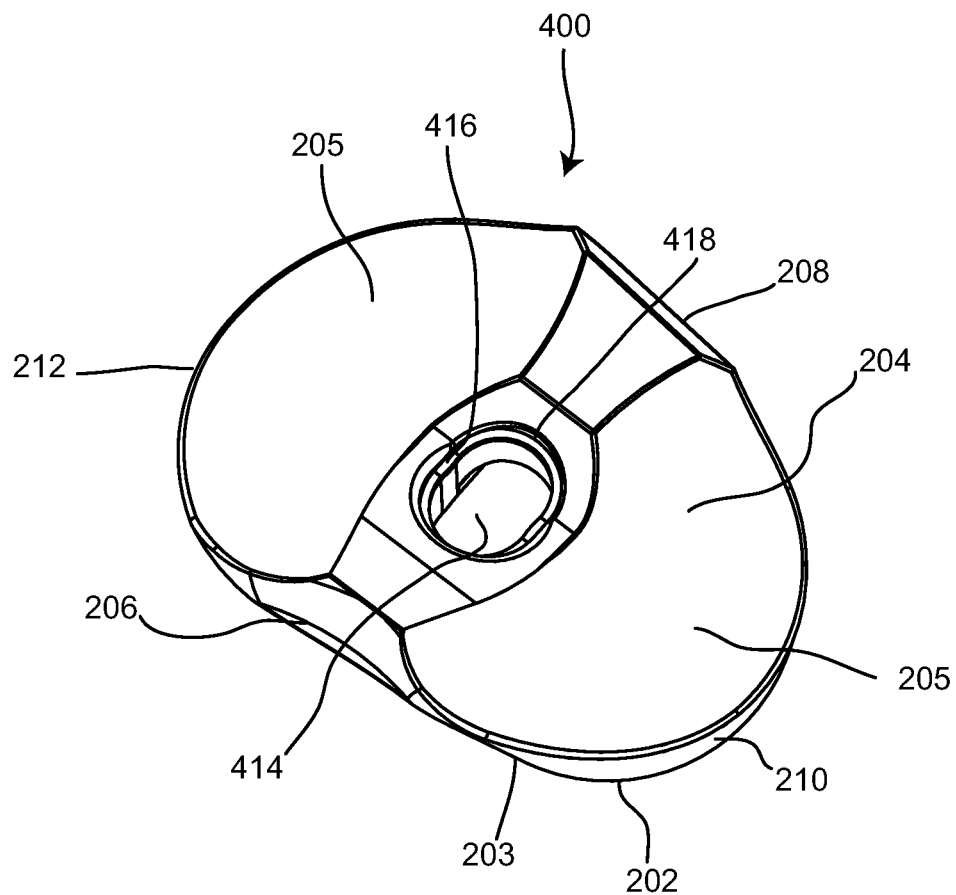
FIG. 10 is a perspective view of a bearing component according to one alternative embodiment of the invention, which may be used in place of the bearing component of FIG. 4 to provide relative translation as well as rotation between the bearing component and the first component.
Figure 10:
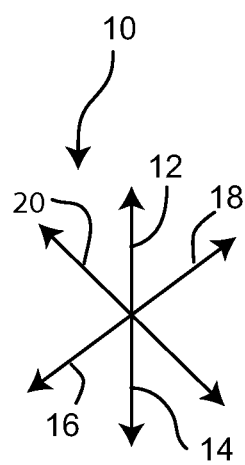

Referring to FIG. 10, a perspective view illustrates a bearing component 400 according to an alternative embodiment of the invention. A bore 414 is generally centrally located, extending through the bearing component 200 from the first component facing side 202 to the third component facing side 204. In the embodiment shown, the bore 414 has an elongated shape, thus allowing translation along with rotation. The elongated shape can either be generally parallel to the medial-lateral axis 20, as shown in FIG. 10, or parallel to anterior and posterior directions 16 and 18, allowing translation and rotation along the major axis of the bearing component 400 relative to the first component 100. In alternative embodiments (not shown), a bore may be shaped to permit both anterior-posterior, and medial-lateral, relative motion between a bearing component and the associated first component. Such embodiments may or may not permit relative rotation between the bearing component and the first component.

The bore 414 is positioned to fit over the post 112 of the first component, allowing the that first component facing side 202 to align with the flat bearing facing side 104 when the bearing component 400 is snapped into engagement (i.e., reversibly attached) with the first component 100. Immediately adjacent to where the bore 414 opens to the third component facing side 204, the diameter of the bore 414 is greater, forming a groove 416. Just below the groove 416 in a distal direction is a rim 418, where the diameter of the bore 414 is wider than in the groove 416. The groove 416 and the rim 418 facilitate retention of the bearing component 400 relative to the first component 100 in a manner similar to that of their counterparts 216, 218 of the bearing component 200 of the previous embodiment.

Figure 11:
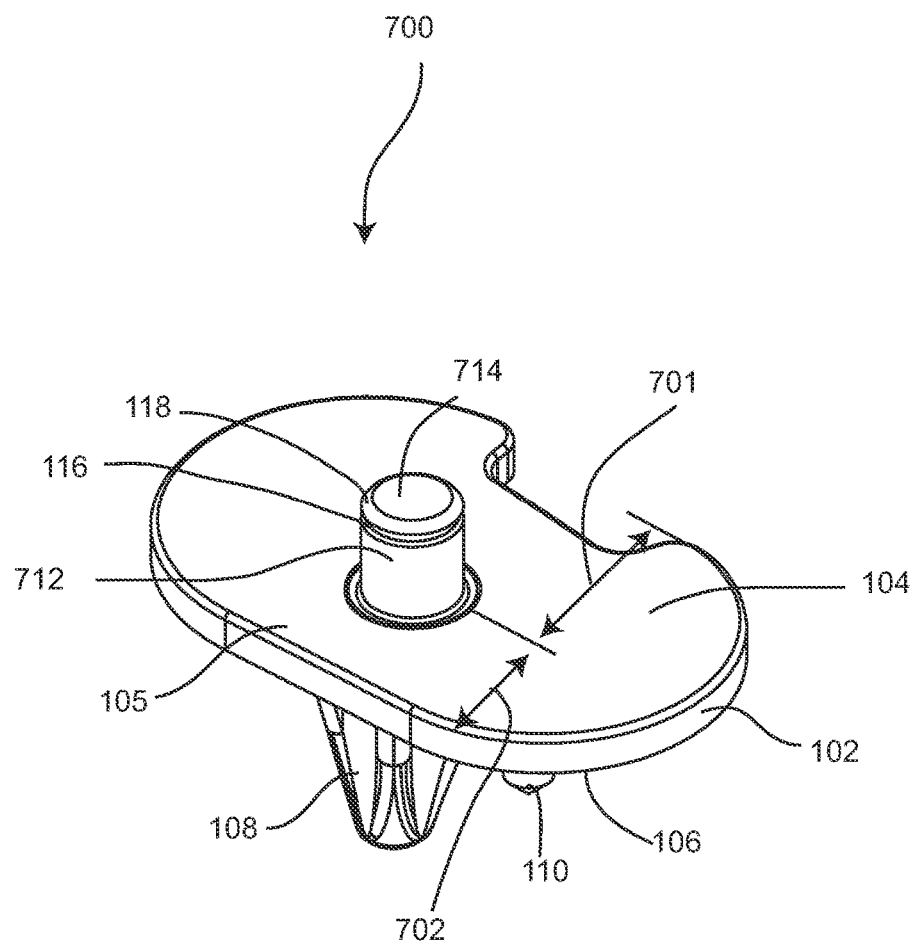
FIG. 11 is a perspective view of a first component according to one alternative embodiment of the invention, which may be used in place of the first component of FIG. 2 to provide a rotation axis offset in the anterior-posterior direction from the geometric center of the first component.
Figure 11:
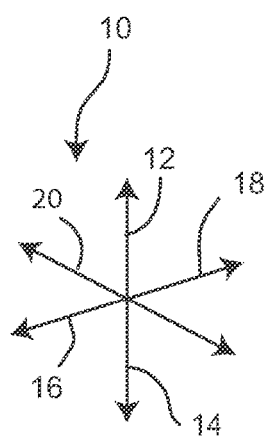

Referring to FIG. 11, a perspective view illustrates a first component 700 according to an alternative embodiment of the invention. The first component 700 comprises an asymmetrical ovoid plate 102 with a flat bearing-facing side 104 and a bone-facing side 106. The bearing-facing side 104 has a first articulating surface 105 which articulates with the bearing insert 200. Extending distally from the bone-facing side 106 is a keel 108, by which the first component 100 is affixed to the prepared bone. In this embodiment of the invention, the keel 108 is offset, in both the anterior-posterior and medial-lateral directions, from the center of the bone-facing side 106 so that it does not extend into the cortical material of the bone. Also extending distally from the bone-facing side 106 is a plurality of pegs 110.

Protruding from the bearing-facing side 104 is a unitary columnar post 512. The post 512 is offset anteriorly to optimize biomechanics such that the anterior distance 502 is less than the posterior distance 501. The post 512 protrudes from the bearing-facing side 104 to a length which is sufficient to retain the bearing component 200, and terminates at a proximal end 514. The unitary columnar post 512 and proximal end 514 constrains movement of the bearing component 200 relative to the first component 500 in a manner similar to that of their counterparts 512 and 514 of the first component 100 of the previous embodiment.

Figure 12:
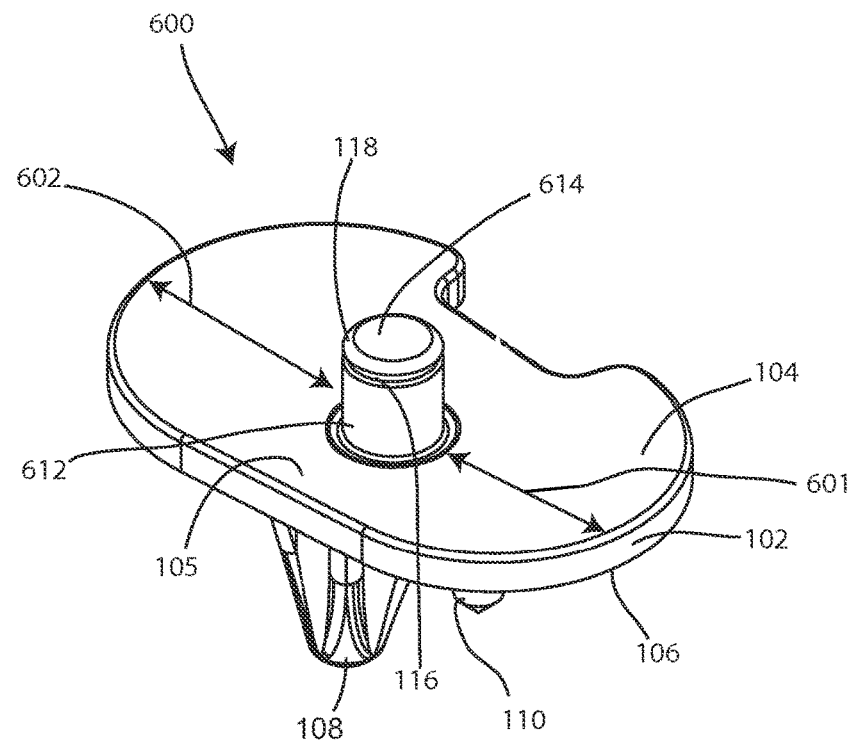
FIG. 12 is a perspective view of a first component according to one alternative embodiment of the invention, which may be used in place of the first component of FIG. 2 to provide a rotation axis offset in the anterior-posterior and medial-lateral direction from the geometric center of the first component.
Figure 12:
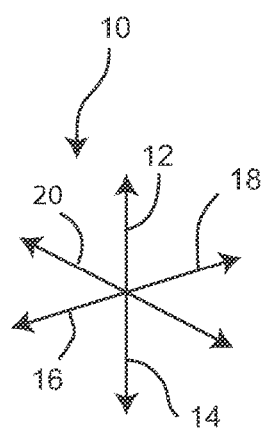

Referring to FIG. 12, a perspective view illustrates a first component 600, according to an alternative embodiment of the invention. The first component 500 comprises a non-symmetrical ovoid plate 102 with a flat bearing-facing side 104 and a bone-facing side 106. The bearing-facing side 104 has a first articulating surface 105 which articulates with the bearing insert 200. Extending distally from the bone-facing side 106 is a keel 108, by which the first component 100 is affixed to the prepared bone. In this embodiment of the invention, the keel 108 is offset, in both the anterior-posterior and medial-lateral directions, from the center of the bone-facing side 106 so that it does not extend into the cortical material of the bone. Also extending distally from the bone-facing side 106 is a plurality of pegs 110.

Protruding from the bearing-facing side 104 is a unitary columnar post 712. The post 712 is offset anteriorly to optimize biomechanics such that the anterior distance 702 is less than the posterior distance 701. The post 712 protrudes from the bearing-facing side 104 to a length which is sufficient to retain the bearing component 200, and terminates at a proximal end 714. The unitary columnar post 712 and proximal end 714 constrains movement of the bearing component 200 relative to the first component 700 in a manner similar to that of their counterparts 112 and 114 of the first component 100 of the previous embodiment.

Referring to FIG. 12, a perspective view illustrates a first component 600, according to an alternative embodiment of the invention. The first component 600 comprises a non-symmetrical ovoid plate 102 with a flat bearing-facing side 104 and a bone-facing side 106. The bearing-facing side 104 has a first articulating surface 105 which articulates with the bearing insert 200. Extending distally from the bone-facing side 106 is a keel 108, by which the first component 100 is affixed to the prepared bone. In this embodiment of the invention, the keel 108 is offset, in both the anterior-posterior and medial-lateral directions, from the center of the bone-facing side 106 so that it does not extend into the cortical material of the bone. Also extending distally from the bone-facing side 106 is a plurality of pegs 110.

Protruding from the bearing-facing side 104 is a unitary columnar post 612. The post 612 is offset both anteriorly and medial-laterally to optimize biomechanics such that, in addition to the anterior offset illustrated in FIG. 11, the medial distance 602 is larger than lateral distance 601. An alternative embodiment (not shown) includes a post offset only in the medial-lateral direction 20. The post 612 protrudes from the bearing-facing side 104 to a length which is sufficient to retain the bearing component 200, and terminates at a proximal end 614. The unitary columnar post 612 and proximal end 614 constrains movement of the bearing component 200 relative to the first component 600 in a manner similar to that of their counterparts 112 and 114 of the first component 100 of the previous embodiment.

The invention claimed is:

1. An orthopaedic prosthesis comprising:
   a first component comprising a base with a keel and a peg protruding from the base to extend into a first bone, wherein the keel is longer than the peg, the keel having a longitudinal axis, and the keel anterior-posteriorly and medial-laterally offset from a geometric center of the base, the base having a first articular surface; and
   a bearing component comprising a second articular surface shaped to articulate with the first articular surface, and a third articular surface shaped to articulate with a fourth articular surface on a second bone;
   wherein the first component further comprises a unitary columnar post extending upward from the first articular surface, the post comprising a groove and a ridge, with the groove positioned below the ridge;
   wherein the bearing component further comprises an anterior end, a posterior end, and a bore extending from the second articular surface through the bearing component to the third articular surface, wherein the diameter of the bore is greater immediately adjacent the third articular surface, the greater diameter of the bore forming a groove;
   wherein the bearing component further comprises a channel formed in the second articular surface of the bearing component, the channel opening on the posterior end of the bearing component and extending from the posterior end of the bearing component to the bore, the channel being ramped such that the depth of the channel varies from the posterior end of the bearing component to the bore;
   wherein a deformable rim is positioned below the groove, within the bore, the rim extending radially toward a center of the bore;
   wherein the deformable rim of the bearing component is positioned in the groove of the first component and the ridge of the first component is positioned in the groove of the bearing component so as to form a releasable connection between the first component and the bearing component;
   wherein the first component and the bearing component are configured such that the bearing component is vertically securable onto the first component without requiring translational movement of the bearing component relative to the first component so that the second articulating surface of the bearing component engages the first articulating surface of the first component;
   and further wherein the unitary columnar post of the first component and the bore of the bearing component are configured such that, when the deformable rim of the bore of the bearing component is positioned in the groove of the unitary columnar post of the first component and the ridge of the unitary columnar post of the first component is positioned in the groove of the bore of the bearing component, the bearing component is rotatable, but not translatable, relative to the first component.

2. An orthopaedic prosthesis as recited in claim 1, wherein the first bone comprises a tibia, the second bone comprises a femur, and the orthopaedic prosthesis comprises a knee prosthesis, the first component comprising a tibial component of the knee prosthesis, wherein the unitary columnar post has a longitudinal axis anterior-posteriorly offset from the geometric center of the base.

3. An orthopaedic prosthesis as recited in claim 2, further comprising a femoral prosthesis securable to the femur, the femoral prosthesis having the fourth articular surface.

4. An orthopaedic prosthesis as recited in claim 1, wherein the bearing component is configured to rotate without translation about a rotation axis relative to the first component.

5. An orthopaedic prosthesis as recited in claim 4, wherein the rotation axis is offset from a geometric center of the base in at least one of the medial-lateral direction and anterior-posterior direction.

6. An orthopaedic prosthesis as recited in claim 1, wherein the bearing component further comprises an instrument slot depressed in the second articular surface.

7. An orthopaedic prosthesis as recited in claim 1, wherein the keel has a longitudinal axis medial-laterally offset from the geometric center of the base, wherein the keel and the peg comprise a porous material that encourages bone ingrowth; and
   the bearing component comprises a distraction feature shaped to provide at least one of alignment and distraction between the first articular surface and the fourth articular surface during insertion of the bearing component into a joint space between the first and second bones.

8. An orthopaedic prosthesis comprising:

a first component securable to a first bone, the first component comprising a first articular surface and a unitary columnar post, wherein the unitary columnar post comprises a central axis anterior-posteriorly offset from a geometric center, wherein the unitary columnar post further comprises a groove and a ridge, with the groove positioned below the ridge, wherein the first component further comprises a keel comprising a longitudinal axis anterior-posteriorly and medial-laterally offset from the geometric center;

a bearing component comprising a second articular surface shaped to articulate with the first articular surface and a third articular surface shaped to articulate with a fourth articular surface on a second bone, the bearing component further comprising a bore extending from the second articular surface through the bearing component to the third articular surface; wherein a diameter of the bore is greater immediately adjacent the third articular surface, the greater diameter of the bore forming a groove;

wherein the bearing component further comprises an anterior end, a posterior end, a channel formed in the second articular surface of the bearing component, the channel opening on the posterior end of the bearing component and extending from the posterior end of the bearing component to the bore, the channel being ramped such that the depth of the channel varies from the posterior end of the bearing component to the bore, and a cutout extending away from the channel in a medial-lateral direction from the channel;

wherein a deformable rim is positioned below the groove within the bore, the rim extending radially toward a center of the bore;

wherein the deformable rim of the bearing component is positioned in the groove of the first component and the ridge of the first component is positioned in the groove of the bearing component so as to form a releasable connection between the first component and the bearing component, and so as to constrain articulation between the first articular surface and the second articular surface;

wherein the first component and the bearing component are configured such that the bearing component is vertically securable onto the first component without requiring translational movement of the bearing component relative to the first component so that the second articulating surface of the bearing component engages the first articulating surface of the first component;

and further wherein the unitary columnar post of the first component and the bore of the bearing component are configured such that, when the deformable rim of the bore of the bearing component is positioned in the groove of the unitary columnar post of the first component and the ridge of the unitary columnar post of the first component is positioned in the groove of the bore of the bearing component, the bearing component is rotatable, but not translatable, relative to the first component.

9. An orthopaedic prosthesis as recited in claim 8, wherein the first bone comprises a tibia, the second bone comprises a femur, and the orthopaedic prosthesis comprises a knee prosthesis, the first component comprising a tibial component of the knee prosthesis.

10. An orthopaedic prosthesis as recited in claim 9, further comprising a femoral prosthesis securable to the femur, the femoral prosthesis having the fourth articular surface.

11. An orthopaedic prosthesis as recited in claim 8, wherein the bearing component is configured to rotate without translation about a rotation axis relative to the first component.

12. An orthopaedic prosthesis as recited in claim 11, wherein the rotation axis is offset from the geometric center of the base in at least one of the medial-lateral direction and anterior-posterior direction.

13. An orthopaedic prosthesis as recited in claim 8, wherein the bearing component further comprises an instrument slot depressed in the second articular surface.

14. An orthopaedic prosthesis as recited in claim 8, wherein the bearing component comprises a distraction feature shaped to provide at least one of alignment and distraction between the first articular surface and the fourth articular surface during insertion of the bearing component into a joint space between the first and second bones.

* * * * *